United States Patent [19]
Baxter

[11] 4,267,177
[45] May 12, 1981

[54] β-LACTAM ANTI-BACTERIALS, COMPOSITIONS CONTAINING THEM, A PROCESS FOR THEIR PREPARATION, AND METHODS OF USE THEREOF

[75] Inventor: Andrew J. G. Baxter, Hull, England

[73] Assignee: Beecham Group Limited, England

[21] Appl. No.: 68,898

[22] Filed: Aug. 23, 1979

[30] Foreign Application Priority Data

Aug. 25, 1978 [GB] United Kingdom ............... 34643/78

[51] Int. Cl.³ ................ C07D 521/00; A61K 31/545; A61K 31/44; C07D 401/14
[52] U.S. Cl. .................................... 424/246; 424/263; 424/271; 546/272
[58] Field of Search ................ 546/272; 424/263, 271, 424/246

[56] References Cited
U.S. PATENT DOCUMENTS 4,172,144  10/1979  Bouffard et al. ..................... 546/272

FOREIGN PATENT DOCUMENTS 1627  5/1979  European Pat. Off. ................. 546/272
1628  5/1979  European Pat. Off. ................. 546/272

Primary Examiner—Robert T. Bond

[57] ABSTRACT

The compounds of the formula (II):

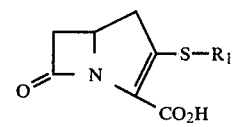

and salts and esters thereof wherein $R_1$ is a pyridyl group optionally substituted by one of two lower alkyl groups or lower acyloxy group, have been found to be antibacterial-agents. Their preparation and use is described.

65 Claims, No Drawings

β-LACTAM ANTI-BACTERIALS, COMPOSITIONS CONTAINING THEM, A PROCESS FOR THEIR PREPARATION, AND METHODS OF USE THEREOF

The present invention relates to β-lactam anti-bacterials, to compositions containing them, to the process for their preparation and to compounds useful as intermediates in that process.

Belgian Patent No. 860962 discloses a vast group of compounds of the general formula (I):

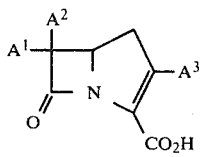
(I)

and their salts and esters wherein $A^1$, $A^2$ and $A^3$ may be hydrogen or various optionally substituted hydrocarbon groups. The activity of these compounds was not illustrated. A further and considerably different group of carbapenems has now been discovered which carry a thioether moiety on the 5-membered ring. These compounds have proved to possess gram-negative and gram-positive antibacterial activity so that they are of interest as broad spectrum antibacterial agents.

The present invention provides the compounds of the formula (II):

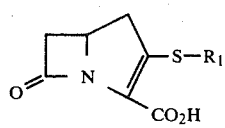
(II)

and salts and esters thereof wherein $R_1$ is a pyridyl group optionally substituted by one or two lower alkyl groups or lower acyloxy group.

When used herein the term "lower" means the group contains up to 4 carbon atoms. When used herein the term "lower alkyl" more suitably means a group of up to 4 carbon atoms which is most suitably a straight chain group.

Suitably $R_1$ is a pyridyl group. More suitably $R_1$ is a 2-pyridyl group.

The compounds of the formula (II) tend to be more active than corresponding esters and are thus particularly suitable.

Compounds of the formula (II) which are esterified have activity in their own right but less than the corresponding acids so in general it is preferred that esters of this invention are those which are convertible to a corresponding salt by chemical or biological means.

Suitably the acid esterified by a group of the sub-formulae (a), (b), (c) or (d):

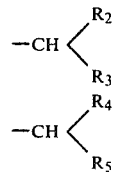

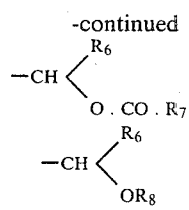

wherein $R_2$ is a hydrogen atom or an alkyl, alkanyl or alkynyl group of up to 3 carbon atoms; $R_3$ is a hydrogen atom or a methyl group; $R_4$ is a phenyl group or a phenyl group substituted by a fluorine, chlorine or bromine atom or a nitro, methyl or methoxyl group; $R_5$ is a hydrogen atom or a phenyl group or a phenyl group substituted by a fluorine, chlorine or bromine atom or a nitro, methyl or methoxyl group; $R_6$ is a hydrogen atom or a methyl group and $R_7$ is a lower alkyl, phenyl or lower alkoxy group or $R_6$ is joined to $R_7$ to form a phthalidyl group; and $R_8$ is a lower alkyl, phenyl, chlorophenyl or nitrophenyl group.

Favourably $R_2$ is a hydrogen atom or a methyl, ethyl, or vinyl group. Favourably $R_3$ is a hydrogen atom. Favourably $R_4$ is a phenyl, p-bromophenyl, p-methoxyphenyl or p-nitrophenyl group. Favourably $R_5$ is a hydrogen atom. Favourably $R_7$ is a methyl, t-butyl or ethoxyl group or is joined to $R_6$. Favourably $R_8$ is a methyl group.

Particularly apt groups of the sub-formula (a) include the methyl and ethyl groups.

Particularly apt groups of the sub-formula (b) include the benzyl and p-nitrobenzyl groups.

Particularly apt groups of the sub-formula (c) include the acetoxymethyl, pivaloyloxymethyl, α-ethoxycarbonyloxyethyl and phthalidyl groups.

A particularly apt group of the sub-formula (d) is the methoxymethyl group.

A preferred esterifying group is p-nitrobenzyl.

A further preferred esterifying group is the phthalidyl group.

The compounds of the formula (II) are generally provided as mixtures of 5R and 5S forms.

This invention also provides an antibacterial pharmaceutical composition which comprises a compound of the formula (II) or a salt or ester thereof and a pharmaceutically acceptable carrier.

Most suitably the composition will comprise the compound of the formula (II) per se.

Most suitably the composition will be in unit dosage form and will comprise 25–1000 mg and more usually 50–500 mg. of a compound of the formula (II).

The compositions of this invention may beneficially also comprise a penicillin or cephalosporin. Certain particularly suitable penicillins for use in these compositions include amoxycillin trihydrate and sodium amoxycillin.

The compositions of this invention may be used for the treatment of bacterial infections due to susceptible bacteria such as gram-positive bacteria such as *Staphylococcus aureus* or gram-negative bacteria such as *Escherichia coli* or *Klebsiella aerogenes*.

The compositions may be administered in conventional manner, for example, orally or parenterally or in cattle by intramammary administration (for the treatment of mastitis).

The compositions may be formulated as described in Belgian Patent Specification No. 860962 or U.S. Ser. Nos. 887,841 or 887,844 the disclosures of which with respect to compositions are included herein by reference.

The compounds of the present invention may be prepared by reaction sequences such as those outlined in the following Scheme.

Scheme

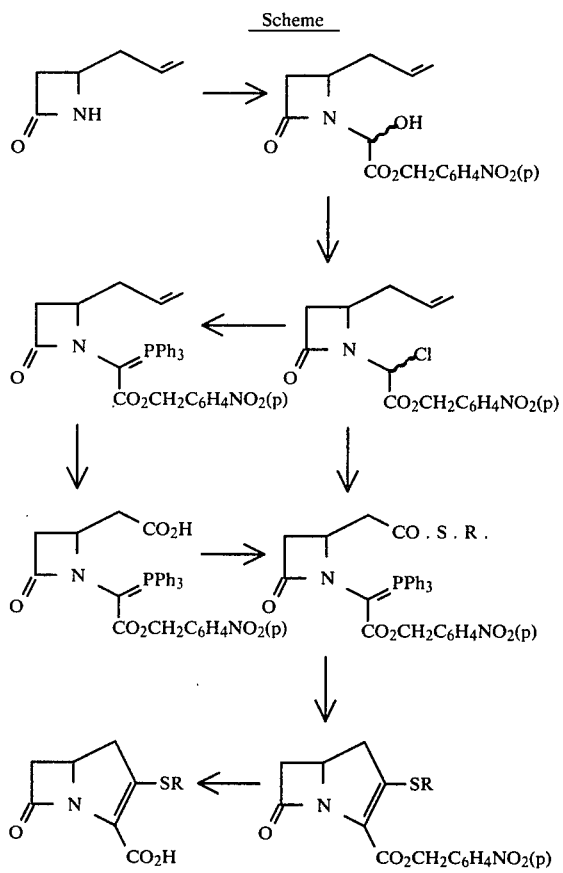

The present invention also provides a process for the preparation of the compounds of this invention which process comprises the ring closing elimination of the elements of triphenylphosphine oxide from an ester of a compound of the formula (III):

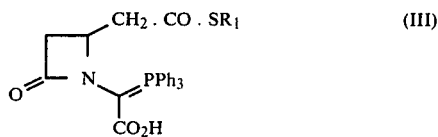

wherein $R_1$ is as defined in relation to formula (II) and thereafter if desired (a) isolating the ester thus produced, (b) where desired de-esterifying a cleavable ester to form a free acid or its salt, (c) optionally converting the salt so formed into a free acid or optionally converting the acid so formed into a salt, and (d) optionally converting a salt into an alternative ester.

The ring closure in normally brought about by heating the ester of the compound of the formula (III) in an inert solvent; for example temperatures of 90°–120° C. and more suitably 100°–110° C. may be employed in a solvent such as toluene or the like. The reaction is best carried out under dry conditions under an inert gas.

The ester of the compound (II) produced may be isolated by any standard method such as fractional crystallisation, counter current separation or chromatography. We have found that it is most convenient to separate the desired product by column chromatography.

Any convenient ester may be used in the process of this invention. Since it is frequently desirable to form a salt of compounds (II), the ester employed is preferably one which is readily converted to the parent acid or its salt by mild methods of hydrogenolysis. In a further aspect therefore the invention includes a process for preparing a salt or free acid of a compound (II) which process comprises de-esterifying an ester of a compound of formula (II). Particularly suitable esters for use in this process include benzyl esters, optionally substituted in the para position by a lower alkoxy, or nitro group or a halogen atom.

A preferred ester for use in this process is the p-nitrobenzyl ester.

Esters of compounds (II) may be de-esterified by conventional methods of hydrogenolysis.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in any inert solvent in which the ester is soluble such as aqueous dioxan or the like. If this hydrogenation is carried out in the presence of a base then a salt of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4O\text{-}COCH_3$, pH7 phosphate buffer. If no base is present, which is preferred, then hydrogenation leads to the preparation of an acid within formula (II). The acid may later be neutralised if desired to yield a salt. Suitable bases which may be used to neutralise acids within formula (II) include LiOH, NaOH, $NaHCO_3$, KOH, $Ca(OH)_2$ and $Ba(OH)_2$.

The salts of acids (II) may be converted to esters in conventional manner, for example by reaction with a reaction halide such as bromophthalide in solution in dimethylformamide or like solvent.

The ester of the compound of the formula (II) may be prepared by the reaction of a corresponding ester of a compound of the formula (IV):

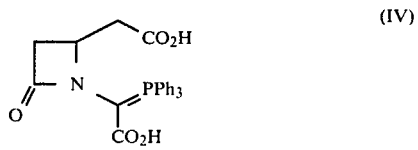

with a diloweralkylphosphorochloridate or thionylchloride and a triloweralkylamine followed by reaction with a thallium I, silver lithium or sodium salt of the compound of the formula (V) in the presence of an organic base.

Preferably the compound of the formula (V) is used in the form of its thallium (I) or lithium salt.

Organic bases for use together with the compound of the formula (V) are preferably tertiary amines such as triloweralkylamines or aromatics bases such as pyridine.

A particularly suitable diloweralkylphosphorochloridate is diethylphosphorochloridate.

A particularly suitable triloweralkylamine is triethylamine. Pyridine is also particularly suitable.

The reaction is generally carried out in an inert organic solvent such as tetrahydrofuran or autonitrile at a non-extreme temperature such as 0° to 40° C. for example 15°–25° C.

The ester of the compound of the formula (IV) may be prepared by the reaction of an ester of the compound of the formula (VI):

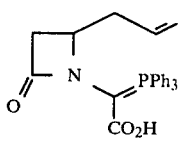
(VI)

with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The ester of the compound of the formula (VI) may be prepared from the corresponding ester of the compound of the formula (VII) by reaction with triphenylphosphine:

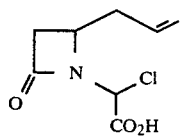
(VII)

This reaction is normally effected in the presence of at least one equivalent of a base of relatively low nucleophilicity such as 2,6-lutidine at an ambient temperature in a dry solvent such as dioxan, tetrahydrofuran or the like.

The ester of the compound of the formula (VII) may be prepared from the corresponding ester of the carbinol of the formula (VIII):

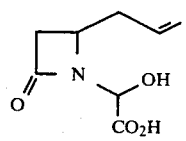
(VIII)

by reaction with thionyl chloride.

This reaction is also normally effected in the presence of at least one equivalent of a base of relatively low nucleophilicity in a dry solvent such as dioxan or tetrahydrofuran but in this instance the reaction is performed at a depressed temperature, for example −30° to −10° C.

The preceding carbinol may be prepared by the reaction of a compound of the formula (IX):

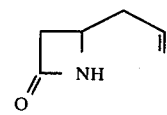
(IX)

with a glyoxylic acid ester.

Normally this reaction is carried out in an inert solvent at an elevated temperature, for example in dry benzene under reflux.

The esters of the compounds of the formula (VIII) may also be prepared by esterification of a salt of the compound of the formula (VIII) in conventional manner. Suitable methods include the reaction of alkali metal salt such as a sodium or potassium salt with a reactive halide or sulphonate ester such as a bromide, chloride, mesylate, tosylate or the like. Such esterifications may be carried out under conventional conditions, for example in dimethylformamide at room temperature.

The salt of compound of the formula (VIII) may be prepared by neutralisation of the acid of the formula (VIII), for example with an alkali metal carbonate or bicarbonate, for example sodium or potassium carbonate.

The compound of formula (VIII) may be prepared by the reaction of glyoxylic acid with the compounds of the formula (IX) as hereinbefore defined.

Intermediates useful for the synthesis of compounds of this invention are available from the processes described in:

British Cognate Application No. 11747/77–11749/77
French Application No. 78/07950
West German Application No. 2811514.2
Japanese Application No. 32804/78
United States Application Ser. No. 887,844
United States Application Ser. No. 887,841
Belgian Patent No. 860962
European Patent Application Publication No. 0002564
European Patent Application Publication No. 0000828

The following Examples illustrate the invention:

EXAMPLE 1

Benzyl 3-(2-pyridylthio)-7-oxo-1-azabicyclo-[3.2.0]hept-2-ene-2-carboxylate

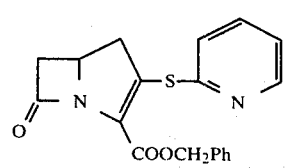

(i) Preparation of 1-(1-benzyloxycarbonyl-1-triphenylphosphoranylidenemethyl)-4-(2-pyridylthiocarbonylmethyl)azetidin-2-one

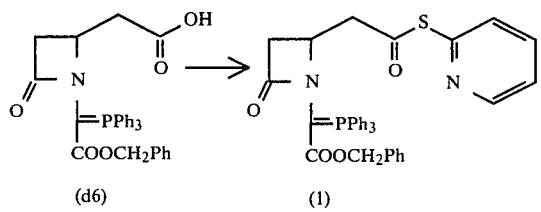

To the phosphorane acid (d6) (0.805 g) in acetonitrile (20 ml) was added dimethylformamide (6 drops) followed by thionyl chloride (0.11 ml). The mixture was stirred for 2 hours at room temperature under argon. Pyridine (0.15 ml) was added, followed by 2-mercaptopyridine (0.17 g). After stirring for 1 hour, the solvent was removed in vacuo and the residue dissolved in ethyl acetate (100 ml) and sat. sodium bicarbonate solution (100 ml). The layers were separated and the organic layer was dried (MgSO₄). Removal of the solvent under reduced pressure, followed by chromatography on silica eluting with ethylacetate-pet. ether mixtures gave the phosphorane (1) as a solid (0.4 g). Recrystallization from ethyl acetate-pet. ether gave pure phosphorane (1) (0.37 g) m.p. 141°–144° having $\nu_{max}$(CHCl₃) 3000, 1740, 1710, 1620 and 1100 cm⁻¹ (Found: C, 70.2; H, 4.90; N, 4.50. $C_{37}H_{31}N_2O_4PS$ requires C, 70.5; H, 4.45%).

(ii) Preparation of benzyl 3(2-pyridylthio)-7-oxo-1-azabicyclo[3.2.0]hept-2-ene-2-carboxylate

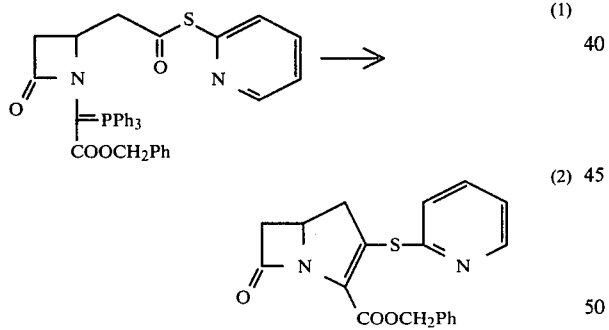

The phosphorane (1) (0.07 g) was dissolved in dry toluene (70 ml) and the solution was degassed under low vacuum. The solution was then heated under reflux for 1½ hours. Removal of solvent and chromatography on silica eluting with pet. ether-ethyl acetate mixtures gave the product (2) (0.007 g) as a yellow oil having $\nu_{max}$ (CHCl₃) 3000, 1790, 1710, 1620, 1280 and 1120 cm⁻¹; $\lambda_{max}$ 320, 298 nm; δ (CDCl₃) 2.89 (1H, dd, J3, 16 Hz, C6-H$_A$), 3.00 (1H, dd, J9, 18 Hz, C4-H$_A$), 3.12 (1H, dd, J9, 18 Hz, C4-H$_B$), 3.44 (1H, dd, J6, 16 Hz, C6-H$_B$), 4.18 (1H, ddt, J3, 6, 9 Hz, C5-H), 5.31 (2H, s, CH₂Ph)), 7.1–7.6 (8H, m, Ph and pyridyl C3, 4 and 5-H) and 8.54 (1H, m, pyridyl C6-H).

The minimum inhibitory concentrations of this compound to inhibit the growth of the following bacteria are:

| Organism | μg/ml (agar + 10% Horse Blood) |
|---|---|
| B. subtilis A | 1.0 |
| E. coli JT20R+ | 100 |
| Citrobacter freundii E8 | 10 |
| Enterobacter cloacae N1 | 100 |
| E. coli 0111 | 2.5 |
| Klebsiella aerogenes A | 2.5 |
| Proteus mirabilis C977 | 10 |
| Proteus morganii 1580 | 10 |
| Proteus rettgeri WM16 | 10 |
| Proteus vulgaris W091 | 50 |
| Ps. aeruginosa A | 100 |
| Salmonella typhimurium CT10 | 2.5 |
| Serratia marcescens US20 | 25 |
| Shigella sonnei MB 11967 | 5.0 |
| Staph. aureus Russell | 5.0 |
| Staph. aureus 1517 | 25 |
| Strep. faecalis I | 100 |
| Strep. pneumoniae | 0.2 |
| Strep. pyogenes CN10 | 0.2 |

EXAMPLE 2 p-Nitrobenzyl 3-(2-pyridylthio)-7-oxo-1-azabicyclo[3.2.0]hept-2-ene-2-carboxylate

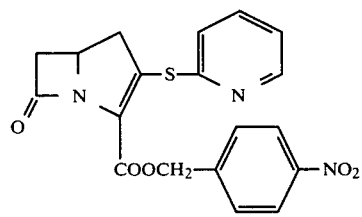

(i) Preparation of 1(p-nitrobenzyloxycarbonyl-1-triphenylphosphoranylidenemethyl)-4(2-pyridylthiocarbonylmethyl)azetidin-2-one

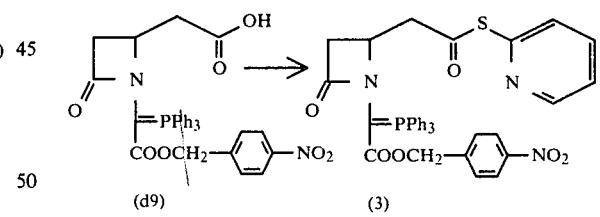

To the phosphorane acid (d9) (2.33 g) in dry tetrahydrofuran (100 ml) was added in turn triethylamine (0.84 ml) and diethyl chlorophosphate (1.04 g) in tetrahydrofuran (2 ml). The mixture was stirred for 3 hours at room temperature in an inert atmosphere. Thallium 2-pyridylthiolate (1.5 g) (prepared from 2-mercaptopyridine and thallous ethoxide in benzene) was added and the reaction mixture stirred for 16 hours. The residue obtained after filtration and removal of solvent was dissolved in ethyl acetate (100 ml) and washed with aqueous sodium bicarbonate solution, water and brine; each aqueous layer being washed once with ethyl acetate (50 ml). The combined organic extracts were dried (MgSO₄) and the solvent was removed under reduced pressure. Chromatography of the crude phosphorane on florisil eluting with 1:1 pet. ether - ethyl acetate to ethyl acetate gave the phosphorane (3) as a yellow solid. Washing with ether followed by recrystallisation from ethyl acetate gave the phosphorane (3) m.p. 169°-172° having $\nu_{max}$ (CHCl$_3$) 3000, 1745, 1710, 1620, 1520, 1435 and 1345 cm$^{-1}$. (Found: C, 65.7; H, 4.30; N, 6.15. C$_{37}$H$_{30}$N$_3$O$_6$PS requires C, 65.8; H, 4.45; N, 6.20%).

(ii) Preparation of p-nitrobenzyl 3-(2-pyridylthio)-7-oxo-1-azabicyclo-[3.2.0]hept-2-ene-2-carboxylate

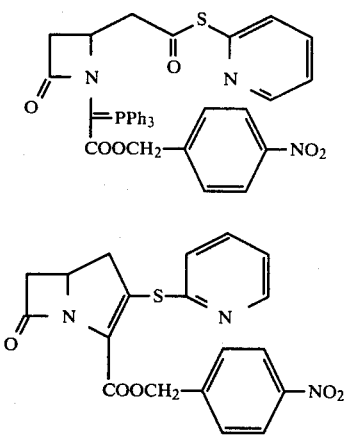

The phosphorane (3) (0.05 g) was dissolved in dry toluene (60 ml) and the solution was degassed under low vacuum. The solution was then heated at reflux under argon for 2¼ hours. Removal of solvent and chromatography on silica eluting with pet. ether - ethyl acetate mixtures gave the product (4) (0.005 g) as a yellow oil having $\nu_{max}$ (CHCl$_3$) 3000, 1790, 1710, 1610, 1520 and 1350 cm$^{-1}$, $\lambda_{max}$ 321 nm.

EXAMPLE 3

Benzyl-3-(3acetoxy-2-pyridylthio)-7-oxo-1-azabicyclo[3.2.0]hept-2-ene-2-carboxylate

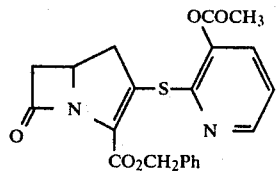

(i) Preparation of 3-acetoxy-2-mercaptopyridine

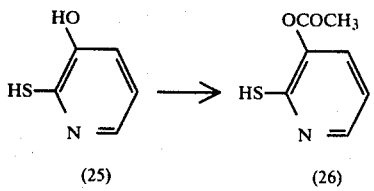

2-Mercapto-3-pyridinol (25) (1.27 g) was dissolved in tetrahydrofuran (50 ml) and treated with acetic anhydride (2 ml) and pyridine (1 ml). The reaction was stirred at room temperature for 48 hours, the solvent evaporated and the residue chromatographed on silica H [Merck Kieselgel 60 (>230 mesh)] to yield 3-acetoxy-2-mercaptopyridine (26) as a yellow crystalline solid from ethyl acetate (0.9 g) m.p. 178°-80°; $\nu_{max}$ (CHCl$_3$) 3400, 1760, 1605, 1590, 1460, 1180 cm$^{-1}$; δ (CDCl$_3$+DMSO-d$_6$) 2.36 (3H, s, COCH$_3$) 6.80 (1H, dd, J18, 20 Hz, CS-H), 7.18 (1H, d) and 7.60 (1H, d,) C4 and C6 H's (Found: C, 49.77; H, 4.16; N, 8.36. C$_7$H$_7$NO$_2$S requires C, 49.70; H, 4.14; N, 8.28%).

(ii) Preparation of 1-(1-benzyloxycarbonyl-1-triphenylphosphoranylidenemethyl)-4-(3-acetoxy-2-pyridinylthiocarbonylmethyl)azetidin-2-one

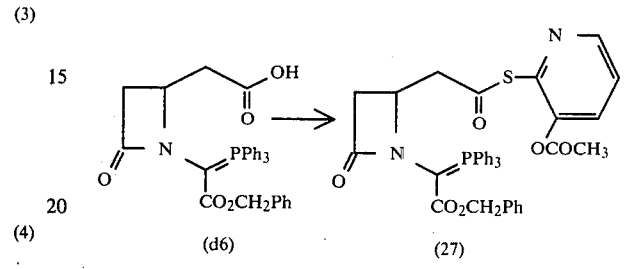

To the phosphorane acid (d6) (1.6 g) in acetonitrile (40 ml) was added dimethylformamide (12 drops) followed by thionyl chloride (0.22 ml). The mixture was stirred at room temperature for 2 hours under argon. Pyridine (0.3 ml) was added followed by 3-acetoxy-2-mercaptopyridine (0.36 g). After stirring for 1 hour the solvent was removed and the residue dissolved in ethyl acetate (100 ml) and saturated sodium bicarbonate solution (100 ml). The organic layer was separated and dried over MgSO$_4$. The solvent was removed on silica H to afford the thiol ester phosphorane (27) as a white solid from ether (0.1 g) m.p. 124°-5°; $\lambda_{max}$ (CHCl$_3$) 1765, 1740, 1620, 1435, 1185, 1105, 1085 cm$^{-1}$.

(iii) Preparation of benzyl-3-(3-acetoxy-2-pyridinylthio)-7-oxo-1-azabicyclo[3.2.0]hept-2-ene-2-carboxylate

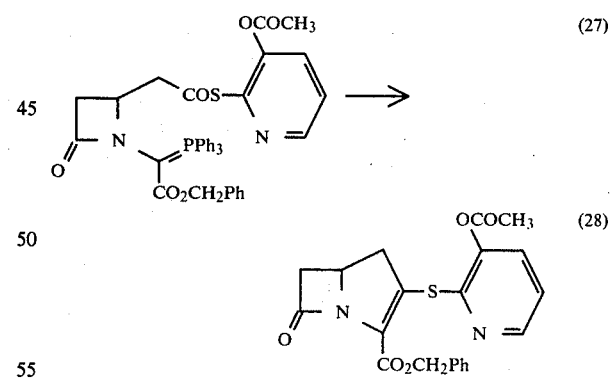

The phosphorane (27) (0.075 g) was dissolved in dry toluene (125 ml) and refluxed under argon for 2½ hours. Evaporation of the solvent and chromatography of the residue on silica H using petroleum ether/ethyl acetate as eluent gave the product (28) as an oil (0.01 g); $\lambda_{max}$ (EtOH) 321 nm; $\nu_{max}$ (CHCl$_3$) 1785, 1775, 1710, 1570, 1410, 1185 cm$^{-1}$; δ(CDCl$_3$) 2.26 (3H, s, COCH$_3$), 2.89 (1H, dd, J17, 3 Hz, C6-Ha), 3.42 (1H, dd, J17, 5.5 Hz, C6-Hb), 2.70–3.60 (2H, complex pattern, C4-CH$_2$), 4.15 (1H, m, C5-H), 5.29 (2H, s, benzyl CH$_2$), 6.80–7.60 (7H, m, Ar and pyridyl C4 and C5-H), 8.40 (1H, m, pyridyl C3-H). The minimum inhibitory concentrations of this compound required to inhibit the growth of the following bacteria are given below:

| Organism | μg/ml (D.S.T. agar + 10% Horse Blood) |
|---|---|
| Citrobacter freundii E8 | 25 |
| Enterobacter cloacae N1 | 50 |
| Escherichia coli 0111 | 50 |
| Klebsiella aerogenes A | 12.5 |
| Proteus vulgaris W091 | 25.0 |
| Salmonella typhimurium MB 11967 | 50.0 |
| Bacillus subtilis | 50.0 |
| Staphylococcus aureus Oxford | 12.5 |
| Streptococcus pneumoniae CN33 | 5.0 |
| Escherichia coli ESS | 5.0 |

EXAMPLE 4

3-(2-Pyridylthio)-7-oxo-1-azabicyclo[3.2.0]hept-2-ene-2-carboxylate

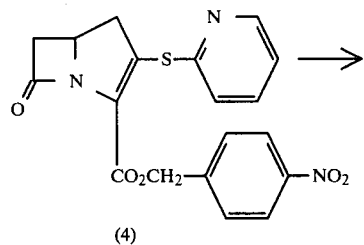

(4)

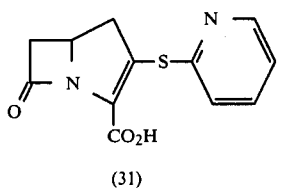

(31)

p-Nitrobenzyl-3-(pyridylthio)-7-oxo-1-azabicyclo[3.2.0]hept-2-ene-2-carboxylate (4) (0.09 g) was dissolved in dioxan (15 ml) to which ethanol (0.75 ml) was added followed by deionised water (2.5 ml) and $M/20$ phosphate buffer (3 ml). To the solution was added 10% Pd/C (0.09 g) and the mixture was hydrogenated at ambient temperature and pressure for 2 hours. The solution was filtered through Kieselguhr and a further quantity of catalyst (85 mg) was added. The hydrogenolysis was continued for a further 1½ hours, the reaction mixture filtered through Kieselguhr, washed with water (5 ml) and extracted with ether (3×10 ml). The aqueous phase contained the product (31) (approximately 0.01 g based on the U.V. absorption); $\lambda_{max}$ (H₂O) 249, 304 nm.

The minimum inhibitory concentrations of this compound required to inhibit the growth of the following bacteria are given below:

| Organism | μg/ml (D.S.T. agar + 10% Horse Blood) |
|---|---|
| Escherichia coli 0111 | 3.1 |
| Escherichia coli ESS | 0.8 |
| Klebsiella aerogenes A | 3.1 |
| Proteus mirabilis C977 | 12.5 |
| Salmonella typhimurium G10 | 3.1 |
| Bacillus subtilis | 1.6 |
| Staphylococcus aureus Oxford | 3.1 |
| Streptococcus pneumoniae CN33 | ≦0.1 |
| Streptococcus pyogenes CN10 | 0.8 |

I claim:
1. A compound of the formula (II):

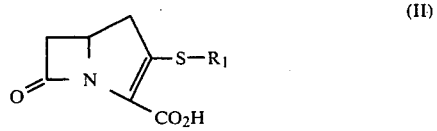

a pharmaceutically acceptable salt thereof or an ester thereof wherein the hydrogen atom of the carboxyl group is replaced by a group of the formula:

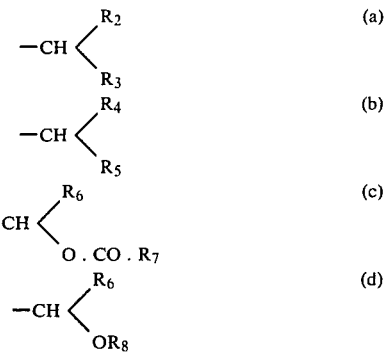

wherein:
R₂ is hydrogen or alkyl, alkenyl or alkynyl each of up to 3 carbon atoms;
R₃ is hydrogen or methyl;
R₄ is phenyl unsubstituted or substituted by fluorine, chlorine, bromine, nitro, methyl or methoxyl;
R₅ is hydrogen or phenyl unsubstituted or substituted by florine, chlorine, bromine, nitro, methyl or methoxyl;
R₆ is hydrogen or methyl;
R₇ is lower alkyl or lower alkoxy of up to 3 carbon atoms, or phenyl; or R₆ is joined to R₇ to form phthalidyl; and
R₈ is lower alkyl of up to 3 carbon atoms, phenyl, chlorophenyl or nitrophenyl, each such ester being de-esterifiable by hydrogenolysis to the acid form of formula (II) and salifiable in conventional manner to pharmaceutically acceptable salt form and R₁ is pyridyl unsubstituted or substituted by one or two lower alkyl or lower alkanoyl of up to 3 carbon atoms.

2. A compound according to claim 1 wherein R₁ is pyridyl.

3. A compound according to claim 1 wherein R₁ is 2-pyridyl.

4. 3-(2-Pyridylthio)-7-oxo-1-azabicyclo[3.2.0]hept-2-ene-2-carboxylate.

5. A compound according to claim 1 which is a mixture of 5R and 5S forms.

6. A compound according to claim 1 in acid form or in the form of a pharmaceutically acceptable salt or a pharmaceutically non-acceptable salt as an intermediate for the pharmaceutically acceptable salt.

7. An ester according to claim 1 which is the phthalidyl ester.

8. An ester according to claim 1 which is the p-nitrobenzyl ester.

9. A compound of the formula (II):

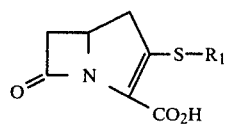

(II)

wherein $R_1$ is pyridyl unsubstituted or substituted by one or two lower alkyl or alkanoyl groups of up to 3 carbon atoms.

10. The compound according to claim 1 which is benzyl 3-(2-pyridylthio)-7-oxo-1-azabicyclo-[3.2.0]hept-2-ene-2-carboxylate.

11. The compound according to claim 1 which is p-nitrobenzyl 3-(2-pyridylthio)-7-oxo-1-azabicyclo[3.2.0]hept-2-ene-2-carboxylate.

12. The compound according to claim 1 which is benzyl-3-(3-acetoxy-2-pyridylthio)-7-oxo-1-azabicyclo[3.2.0]hept-2-ene-2-carboxylate.

13. A compound according to claim 1 in the form of an ester wherein the hydrogen atom of the carboxyl group is replaced by a group of the formula

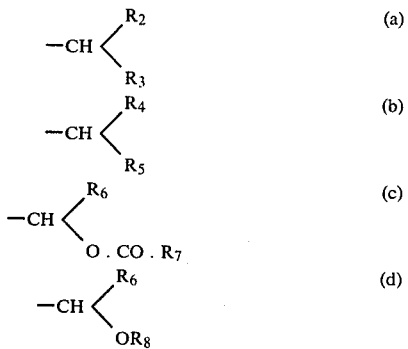

wherein $R_2$ is hydrogen or alkyl, alkenyl or alkynyl, each of up to 3 carbon atoms; $R_3$ is hydrogen or methyl; $R_4$ is phenyl unsubstituted or substituted by fluorine, chlorine, bromine, nitro, methyl or methoxyl; $R_5$ is hydrogen or phenyl unsubstituted or substituted by fluorine, chlorine, bromine, nitro, methyl or methoxyl; $R_6$ is hydrogen or methyl; and $R_7$ is lower alkyl, phenyl or lower alkoxy; or $R_6$ is joined to $R_7$ to form phthalidyl; and $R_8$ is lower alkyl, phenyl, chlorophenyl or nitrophenyl.

14. An ester according to claim 13 wherein $R_2$ is hydrogen, methyl, ethyl or vinyl; $R_3$ is hydrogen; $R_4$ is phenyl, p-bromophenyl, p-methoxyphenyl, p-nitrophenyl; $R_5$ is hydrogen; $R_7$ is methyl, t-butyl or ethoxyl or $R_6$ is joined to $R_7$ to form phthalidyl; and $R_8$ is methyl.

15. An ester according to claim 14 wherein the ester is the methyl or ethyl ester.

16. An ester according to claim 13 wherein the ester is the benzyl or p-nitrobenzyl ester.

17. An ester according to claim 13 wherein the ester is the acetoxymethyl, pivaloyloxymethyl, α-ethoxycarbonyloxyethyl or phthalidyl ester.

18. An ester according to claim 13 wherein the ester is the methoxymethyl ester.

19. An ester according to claim 13 wherein the ester is the p-nitrobenzyl ester.

20. An ester according to claim 13 wherein the ester is the phthalidyl ester.

21. A process for the preparation of a compound according to claim 1 which process comprises the ring closing elimination of the elements of triphenylphosphine oxide from an ester as defined in claim 1 of a compound of the formula (III):

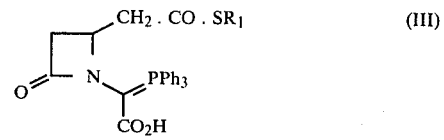

(III)

wherein the hydrogen atom of the carboxyl group is replaced by a said group a), b), c), or d) as defined in claim 1 and $R_1$ is pyridyl unsubstituted or substituted by one or two lower alkyl or lower acyloxy groups of up to 3 carbon atoms, and thereafter optionally (a) isolating such ester thus produced, (b) optionally de-esterifying a such ester by hydrogenolysis to form the free acid or, (c) optionally converting the resulting free acid into a pharmaceutically acceptable salt, and (d) optionally converting such salt into an above-defined ester.

22. A pharmaceutical composition useful for treating bacterial infections in humans and animals which comprises an antibacterially effective amount of a compound of the formula (II):

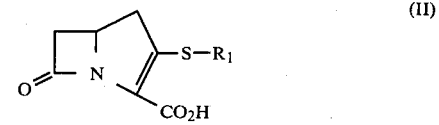

(II)

in its acid form or as a pharmaceutically acceptable salt or ester as defined in claim 1 wherein $R_1$ is pyridyl unsubstituted or substituted by one or two lower alkyl or alkanoyl group of up to 3 carbon atoms, in combination with a pharmaceutically acceptable carrier.

23. A composition according to claim 22 wherein the compound of formula (II) is in the form of a pharmaceutically acceptable ester as defined in claim 1.

24. A composition according to claim 22 wherein $R_1$ is pyridyl.

25. A composition according to claim 22 wherein $R_1$ is 2-pyridyl.

26. A composition according to claim 22 wherein the compound is a mixture of 5R and 5S forms.

27. A composition according to claim 22 wherein the compound is in the form of a pharmaceutically acceptable salt.

28. A composition according to claim 22 in oral administration form.

29. A composition according to claim 22 in parenteral administration form.

30. A composition according to claim 22 useful for treating bacterial infections in cattle, which is in intra mammary administration form.

31. A composition according to claim 22 wherein the compound is benzyl 3-(2-pyridylthio)-7-oxo-1-azabicyclo-[3.20]hept-2-ene-2-carboxylate.

32. A composition according to claim 22 wherein the compound is p-nitrobenzyl 3-(2-pyridylthio)-7-oxo-1-azabicyclo[3.2.0]hept-2-ene-2-carboxylate.

33. A composition according to claim 22 wherein the compound is benzyl-3-(3-acetoxy-2-pyridylthio)-7-oxo-1-azabicyclo[3.2.0]hept-2-ene-2-carboxylate.

34. A composition according to claim 22 wherein the compound is 3-(2-pyridylthio)-7-oxo-1-azabicyclo[3.2.0]hept-2-ene-2-carboxylate.

35. A composition according to claim 22 wherein the compound of formula (II) is in acid, salt or ester form wherein the ester "group which replaces the hydrogen atom of the carboxyl group" is of the formula:

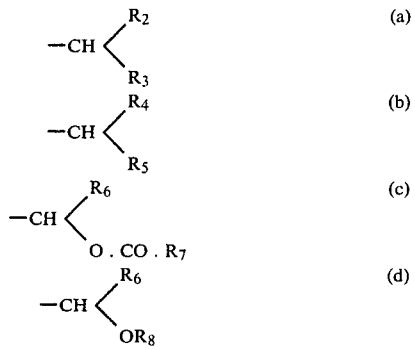

wherein $R_2$ is hydrogen or alkyl, alkenyl or alkynyl each of up to 3 carbon atoms; $R_3$ is hydrogen or methyl; $R_4$ is phenyl unsubstituted or substituted by fluorine, chlorine, bromine, nitro, methyl or methoxyl; $R_5$ is hydrogen or phenyl unsubstituted or substituted by fluorine, chlorine, bromine, nitro, methyl or methoxyl; $R_6$ is hydrogen or methyl; and $R_7$ is lower alkyl of up to 3 carbon atoms, phenyl or lower alkoxy of up to 3 carbon atoms; or $R_6$ is joined to $R_7$ to form phthalidyl; and $R_8$ is lower alkyl of up to 3 carbon atoms, phenyl, chlorophenyl or nitrophenyl.

36. A composition according to claim 35 wherein $R_2$ is hydrogen, methyl, ethyl or vinyl; $R_3$ is hydrogen; $R_4$ is phenyl, p-bromophenyl, p-methoxyphenyl, p-nitrophenyl; $R_5$ is hydrogen; $R_7$ is methyl, t-butyl or ethoxyl or $R_6$ is joined to $R_7$ to form phthalidyl; and $R_8$ is methyl.

37. A composition according to claim 35 wherein the ester is the methyl or ethyl ester.

38. A composition according to claim 35 wherein the ester is the benzyl or p-nitrobenzyl ester.

39. A composition according to claim 35 wherein the ester is the acetoxymethyl, pivaloyloxymethyl, α-ethoxycarbonyloxyethyl or phthalidyl ester.

40. A composition according to claim 35 wherein the ester is the methoxymethyl ester.

41. A composition according to claim 35 wherein the ester is the p-nitrobenzyl ester.

42. A composition according to claim 35 wherein the ester is the phthalidyl ester.

43. A method of treating bacterial infections in humans and animals which comprises administering to a human or animal in need thereof an antibacterially effective amount of a compound of the formula (II):

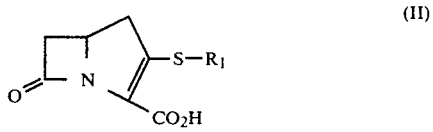

a pharmaceutically acceptable salt thereof or a pharmaceutically acceptable ester thereof wherein the salt or ester is as defined in claim 1, and $R_1$ is pyridyl unsubstituted or substituted by one or two lower alkyl or lower alkanoyloxy groups of up to 3 carbon atoms.

44. A method according to claim 43 wherein $R_1$ is pyridyl.

45. A method according to claim 43 wherein $R_1$ is 2-pyridyl.

46. A method according to claim 43 wherein the compound administered is a mixture of 5R and 5S forms.

47. A method according to claim 43 wherein the compound is administered in a form of a pharmaceutically acceptable salt.

48. A method according to claim 43 wherein the administration is oral.

49. A method according to claim 43 wherein the administration is parenteral.

50. A method according to claim 43 for the treatment of bacterial infections in cattle wherein the administration is intra mammary.

51. A method according to claim 43 wherein the compound is in the form of a pharmaceutically acceptable ester as defined in claim 24.

52. A method according to claim 24 wherein the compound is in the form of an ester of a compound of formula (II), wherein the ester group which replaces the hydrogen atom of the carboxyl group is of the formula:

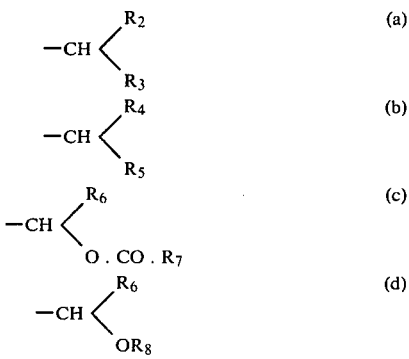

wherein $R_2$ is hydrogen or alkyl, alkenyl or alkynyl each of up to 3 carbon atoms; $R_3$ is hydrogen or methyl; $R_4$ is phenyl unsubstituted or substituted by fluorine, chlorine, bromine, nitro, methyl or methoxyl; $R_5$ is hydrogen or phenyl unsubstituted or substituted by fluorine, chlorine, bromine, nitro, methyl or methoxyl; $R_6$ is hydrogen or methyl; and $R_7$ is lower alkyl of up to 3 carbon atoms, phenyl or lower alkoxy; or $R_6$ is joined to $R_7$ to form phthalidyl and $R_8$ is lower alkyl of up to 3 carbon atoms, phenyl, chlorophenyl or nitrophenyl.

53. A method according to claim 52 wherein $R_2$ is hydrogen, methyl, ethyl or vinyl; $R_3$ is hydrogen; $R_4$ is phenyl, p-bromophenyl, p-methoxyphenyl, p-nitrophenyl; $R_5$ is hydrogen; $R_7$ is methyl, t-butyl or ethoxyl or $R_6$ is joined to $R_7$ to form phthalidyl; and $R_8$ is methyl.

54. A method according to claim 52 wherein the ester is the methyl or ethyl ester.

55. A method according to claim 52 wherein the ester is the benzyl or p-nitrobenzyl ester.

56. A method according to claim 52 wherein the ester is the acetoxymethyl, pivaloyloxymethyl, α-ethoxycarbonyloxyethyl or phthalidyl ester.

57. A method according to claim 52 wherein the ester is the methoxymethyl ester.

58. A method according to claim 52 wherein the ester is the p-nitrobenzyl ester.

59. A method according to claim 52 wherein the ester is the phthalidyl ester.

60. A method according to claim 43 wherein the compound is benzyl 3(2-pyridylthio)-7-oxo-1-azabicyclo-[3.2.0]hept-2-ene-2-carboxylate.

61. A method according to claim 43 wherein the compound is p-nitrobenzyl 3-(2-pyridylthio)-7-oxo-1-azabicyclo [3.2.0]hept-2-ene-2-carboxylate.

62. A method according to claim 43 wherein the compound is benzyl-3-(3-acetoxy-2-pyridylthio)-7-oxo-1-azabicyclo[3.2.0]hept-2-ene-2-carboxylate.

63. A method according to claim 43 wherein the compound is 3-(2-pyridylthio)-7-oxo-1-azabicyclo[3.2.0]hept-2-ene-2-carboxylate.

64. A pharmaceutical composition useful for treating bacterial infections in humans and animals which comprises a synergistically effective amount of a compound of the formula (II):

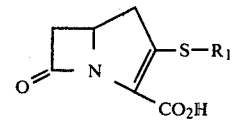

(II)

or a pharmaceutically acceptable salt or ester thereof wherein the salt or ester is as defined in claim 1, and $R_1$ is pyridyl unsubstituted or substituted by one or two lower alkyl or lower-alkanoyloxy group of up to 3 carbon atoms, and an antibacterially effective amount of a penicillin or a cephalosporin, in combination with a pharmaceutically acceptable carrier.

65. A method of treating bacterial infections in humans and animals which comprises administering to a human or animal in need thereof, a synergistically effective amount of a compound of the formula (II):

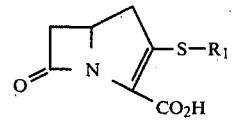

(II)

or a pharmaceutically acceptable salt or ester thereof wherein the salt or ester is as defined in claim 1, and $R_1$ is pyridyl unsubstituted or substituted by one or two lower alkyl or lower alkanoyloxy, and an antibacterialy effective amount of a penicillin or a cephalosporin.

* * * * *